United States Patent
Daerr et al.

(10) Patent No.: US 9,833,202 B2
(45) Date of Patent: Dec. 5, 2017

(54) SYSTEM FOR GENERATING SPECTRAL COMPUTED TOMOGRAPHY PROJECTION DATA

(71) Applicant: KONINKLIJKE PHILIPS N.V., Eindhoven (NL)

(72) Inventors: Heiner Daerr, Hamburg (DE); Roger Steadman Booker, Aachen (DE); Gereon Vogtmeier, Aachen (DE); Ewald Roessl, Henstedt-Ulzburg (DE); Gerhard Martens, Henstedt-Ulzburg (DE); Carolina Ribbing, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/108,401

(22) PCT Filed: Dec. 1, 2015

(86) PCT No.: PCT/EP2015/078113
§ 371 (c)(1),
(2) Date: Jun. 27, 2016

(87) PCT Pub. No.: WO2016/087394
PCT Pub. Date: Jun. 9, 2016

(65) Prior Publication Data
US 2017/0258412 A1 Sep. 14, 2017

(30) Foreign Application Priority Data
Dec. 5, 2014 (EP) ..................................... 14196541

(51) Int. Cl.
*H05G 1/26* (2006.01)
*A61B 6/03* (2006.01)
(Continued)

(52) U.S. Cl.
CPC ................ *A61B 6/032* (2013.01); *A61B 6/06* (2013.01); *A61B 6/4042* (2013.01);
(Continued)

(58) Field of Classification Search
CPC .. A61B 6/00; A61B 6/03; A61B 6/032; A61B 6/035; A61B 6/482; A61B 6/4241;
(Continued)

(56) References Cited

U.S. PATENT DOCUMENTS 4,323,784 A 4/1982 Conrad
6,650,730 B2 11/2003 Bogatu et al.
(Continued)

FOREIGN PATENT DOCUMENTS

JP 4426887 3/2010
JP 2014138660 7/2014
(Continued)

OTHER PUBLICATIONS

Schlomka et al., "Experimental feasibility of multi-energy photon-counting K-edge imaging in pre-clinical computed tomography", Physics in Medicine and Biology, vol. 53, pp. 4031 to 4047 (2008).
(Continued)

*Primary Examiner* — Jurie Yun

(57) ABSTRACT

The invention relates to a system (31) for generating spectral computed tomography projection data. A spectral projection data generation device (6) comprising an energy-resolving detector generates spectral computed tomography projection databased on polychromatic radiation (4), which has been provided by a radiation device (2), after having traversed an examination zone (5), and a reference values generation device generates energy-dependent reference values based on radiation, which has not traversed the examination zone. A spectral parameter providing unit (12) provides a spectral parameter being indicative of a spectral property of the
(Continued)

radiation device based on the energy-dependent reference values. In particular, spectral properties of the radiation device can be monitored over time, wherein this information can be used for, for instance, correcting the spectral computed tomography projection data, and/or, if undesired spectral properties of the radiation device are indicated, triggering a replacement of the radiation device.

15 Claims, 15 Drawing Sheets

(51) Int. Cl.
*A61B 6/00* (2006.01)
*A61B 6/06* (2006.01)

(52) U.S. Cl.
CPC .......... *A61B 6/4078* (2013.01); *A61B 6/4241* (2013.01); *A61B 6/485* (2013.01); *A61B 6/582* (2013.01)

(58) Field of Classification Search
CPC .. A61B 6/06; A61B 6/58; A61B 6/582; A61B 6/586; G01N 23/00; G01N 23/083; G01N 23/087; G01N 23/046; H05G 1/26
USPC .............................. 378/4, 5, 6, 19, 165, 207
See application file for complete search history.

(56) References Cited

U.S. PATENT DOCUMENTS

| | | | |
|---|---|---|---|
| 7,567,646 B2 | 7/2009 | Buchinsky | |
| 7,668,289 B2 | 2/2010 | Proksa et al. | |
| 8,615,120 B2 | 12/2013 | Proksa | |
| 2005/0123090 A1 | 6/2005 | Heismann et al. | |
| 2007/0291898 A1 | 12/2007 | Groves et al. | |
| 2010/0193700 A1 | 8/2010 | Herrmann et al. | |
| 2011/0012014 A1 | 1/2011 | Livne et al. | |
| 2011/0216878 A1 | 9/2011 | Roessl | |
| 2011/0261926 A1 | 10/2011 | Hangartner et al. | |
| 2012/0250822 A1 | 10/2012 | Helm et al. | |
| 2013/0301799 A1 | 11/2013 | Kang et al. | |
| 2014/0072098 A1 | 3/2014 | Kappler | |
| 2014/0119517 A1 | 5/2014 | Lee et al. | |
| 2014/0185758 A1 | 7/2014 | Kang et al. | |

FOREIGN PATENT DOCUMENTS

| | | |
|---|---|---|
| WO | 2012/080927 | 6/2012 |
| WO | 2012/159201 | 11/2012 |
| WO | 2014/027260 | 2/2014 |
| WO | 2014/077283 | 5/2014 |
| WO | 2014/123813 | 8/2014 |
| WO | 2014/128595 | 8/2014 |

OTHER PUBLICATIONS

Steadman, et al., "ChromAIX: Fast photon-counting ASIC for Spectral Computed Tomography", Nuclear Instruments and Methods in Physics Research Section A: Accelerators, Spectrometers, Detectors and Associated Equipment, vol. 648, supplement 1, pp. S211 to S215 (2011).

Rink, et al., "Investigating the feasibility of photon-counting K-edge imaging at high x-ray fluxes using nonlinearity corrections", Med. Phys. 40 (10), Oct. 2013.

Taguchi, et al., "Enabling Photon Counting Clinical X-ray CT", 2009 IEEE Nuclear Science Symposium Conference Record.

SYSTEM FOR GENERATING SPECTRAL COMPUTED TOMOGRAPHY PROJECTION DATA

CROSS REFERENCE TO RELATED APPLICATIONS

This application is the U.S. National Phase application under 35 U.S.C. §371 of International Application No. PCT/EP2015/078113, filed Dec. 1, 2015, published as WO 2016/087394 on Jun. 9, 2016, which claims the benefit of European Patent Application Number 14196541.8 filed Dec. 5, 2014. These applications are hereby incorporated by reference herein.

FIELD OF THE INVENTION

The invention relates to a system and method for generating spectral computed tomography projection data. The invention relates further to a computer program for controlling the system and to a spectral computed tomography system comprising the system for generating spectral computed tomography projection data.

BACKGROUND OF THE INVENTION

US 2014/0072098 A1 discloses an x-ray system comprising an x-ray source for emitting x-ray radiation and a radiation detector for detecting the x-ray radiation after having traversed a subject to be examined. The x-ray system further comprises a monitor detector irradiated by radiation emitted by the x-ray source, which has not traversed the subject, wherein the monitor detector is configured as an energy-resolving detector to provide energy-resolved current dose measurement data representing a current dose of the x-ray radiation.

For generating spectral computed tomography projection data a spectral computed tomography system comprises a radiation device which provides polychromatic radiation traversing a subject to be imaged and a detector which detects the polychromatic radiation after having traversed the subject. The spectral computed tomography system is adapted to generate the spectral computed tomography projection data for different projection directions and to reconstruct a computed tomography image based on the spectral computed tomography projection data.

The spectral properties of the radiation device may vary over time due to, for instance, a roughening of an anode of an x-ray tube of the radiation device, unintended variations of an applied tube voltage, unintended focal spot movements, et cetera. The variations of the spectral properties of the radiation device can result in artifacts in the reconstructed computed tomography image.

SUMMARY OF THE INVENTION

It is an object of the present invention to provide a system and method for generating spectral computed tomography projection data, which allow for an improved quality of computed tomography images. It is a further object of the present invention to provide a computer program for controlling the system and to provide a computed tomography system comprising the system for generating spectral computed tomography projection data.

In a first aspect of the present invention a system for generating spectral computed tomography projection data is presented, wherein the system comprises:

a radiation device for providing polychromatic radiation for traversing an examination zone of the system, a spectral projection data generation device for generating spectral computed tomography projection data based on the radiation after having traversed the examination zone, a reference values generation device for generating energy-dependent reference values based on radiation, which has not traversed the examination zone, and a spectral parameter providing unit for providing a spectral parameter being indicative of a spectral property of the radiation device based on the energy-dependent reference values.

Since energy-dependent reference values are determined based on radiation, which has not traversed the examination zone, and since a spectral parameter being indicative of a spectral property of the radiation device is determined based on the energy-dependent reference values, spectral properties of the radiation device can be monitored over time, wherein this spectral property information can be used for improving the quality of a computed tomography image which is reconstructed based on the spectral computed tomography projection data. For instance, the spectral property information can be used to correct the spectral computed tomography projection data, wherein the corrected spectral computed tomography projection data may be used for reconstructing the computed tomography image, in order to increase the image quality. Or, if the spectral property information indicates undesired spectral properties of the radiation device, the radiation device may be replaced by a radiation device having desired spectral properties which lead to computed tomography images having an improved image quality.

The spectral parameter can be, for instance, a parameter indicating a change in the spectrum of the polychromatic radiation provided by the radiation device over time. The spectral parameter can also define the current spectrum of the polychromatic radiation provided by the radiation device. Generally, the spectral parameter providing unit can be adapted to provide one or several spectral parameters related to the current spectrum and/or a change of the spectrum of the polychromatic radiation. In an embodiment the spectral parameter providing unit can be adapted to directly provide the energy-dependent reference values, which depend on the spectrum of the polychromatic radiation provided by the radiation device, as spectral parameters.

The spectral projection data generation device comprises an energy-resolving detector, especially an energy-resolving photon-counting detector, for generating the spectral computed tomography projection data. The photon-counting detector can comprise a direct-conversion material like Cd(Zn)Te. Moreover, the reference values generation device can comprise an energy-resolving reference detector for generating the energy-dependent reference values. In an embodiment the energy-resolving detector of the spectral projection data generation device and the energy-resolving reference detector are of the same type. For instance, both may be photon-counting detectors, especially photon-counting detectors having a direct-conversion material like Cd(Zn)Te. If the energy-resolving detector used for generating the spectral computed tomography projection data and the energy-resolving reference detector are of the same type, it can be assumed that the energy-dependent reference values and the spectral computed tomography projection data are at least partly generated in the same way. The energy-dependent reference values may therefore be well-suited for correcting the spectral computed tomography projection data in accordance with the current spectral properties of the radiation device, which in turn can lead to a further improved quality of a finally reconstructed computed tomography image.

Spectral computed tomography projection data are energy-dependent projection data which have been generated in different acquisition directions. The system for generating spectral computed tomography projection data is therefore preferentially adapted to acquire spectral projections in different acquisition directions with respect to a subject to be examined, which is to be placed within the examination zone. In particular, the system for generating spectral computed projection data is adapted to move the radiation device and optionally also the energy-resolving detector relative to the subject to be examined for generating the spectral computed tomography projection data, especially to move the radiation device and optionally also the energy-resolving detector around the subject along a circular or helical trajectory, in order to acquire the spectral projections in different acquisition directions.

In an embodiment the radiation device comprises a radiation source for emitting the polychromatic radiation and a collimator for collimating the emitted polychromatic radiation, wherein the energy-resolving reference detector is arranged between the radiation source and the collimator. In particular, the reference values generation device may comprise at least two reference detectors arranged between the radiation source and the collimator, wherein at least one of these reference detectors is an energy-resolving reference detector. For instance, the reference values generation device may comprise two energy-resolving reference detectors arranged between the radiation source and the collimator at opposing sides of the opening of the collimator, through which the radiation passes.

The reference values generation device may comprise a K-edge element having a K-edge at an energy within the spectrum of the polychromatic radiation provided by the radiation device, wherein the reference values generation device and the radiation device are arranged such that polychromatic radiation emitted by the radiation device impinges on the K-edge element, wherein the reference values generation device is adapted to generate the energy-dependent reference values based on the radiation coming from the K-edge element. Moreover, the reference values generation device may comprise an energy-resolving reference detector, wherein the reference values generation device and the radiation device may be arranged such that the radiation, which has traversed the K-edge element and hence which has been filtered by the K-edge element, is detectable by the energy-resolving reference detector, wherein the energy-resolving reference detector is adapted to generate the energy-dependent reference values based on the detected radiation. In particular, the reference values generation device may comprise several K-edge elements with K-edges at different energies, which are within the spectrum of the polychromatic radiation provided by the radiation device, for filtering the radiation before being detected by the energy-resolving reference detector. The energy-resolving reference detector preferentially comprises a detection surface, which is sensitive to the radiation emitted by the radiation device, wherein the K-edge materials are arranged side-by-side and/or on top of each other on the detection surface. The spectral parameter providing unit may be adapted to a) determine the spectral parameter based on the spectral reference values at the energies, at which the K-edges are present, and/or b) calculate one or several summed values by summarizing spectral reference values for energies being smaller than the lowest energy, at which a K-edge is present, and/or for energies between energies, at which different K-edges are present, and/or for energies being larger than the largest energy, at which a K-edge is present, and to determine the spectral parameter based on the one or several summed values. For instance, the spectral parameter providing unit can be adapted to determine the spectral parameter based on ratios of spectral reference values at different energies, at which the K-edges are present. Moreover, the spectral parameter providing unit can be adapted to determine the spectral parameter based on ratios of summed values. For instance, the ratios of the summed values and/or the ratios of the spectral reference values at different energies, at which the K-edges are present, can be determined for different times and the ratios determined for different times can be compared, in order to determine a spectral parameter which is indicative of a change of the spectrum of the polychromatic radiation over time. This allows for a very accurate determination of a change of the spectral properties of the radiation device over time.

The reference values generation device may be adapted to generate energy-dependent reference values for different positions and/or times, wherein the spectral parameter providing unit may be adapted to calculate as the spectral parameter a spatial and/or temporal distribution of energy-dependent reference values based on the generated energy-dependent reference values. In particular, the reference values generation device can comprise several energy-resolving reference detectors arranged at different positions, wherein each energy-resolving reference detector is adapted to detect the radiation, which has not traversed the examination zone, and to generate the energy-dependent reference values depending on the detected radiation, and wherein the spectral parameter providing unit is adapted to calculate as the spectral parameter a spatial distribution, which is preferentially also a temporal distribution, of energy-dependent reference values based on the generated energy-dependent reference values. For instance, by extrapolation and/or interpolation energy-dependent reference values for positions, at which the energy-resolving reference detectors are not arranged, and/or for times, for which energy-dependent reference values have not been determined, can be determined and used for calculating a spatial and/or temporal distribution of energy-dependent reference values. The spectral parameter providing unit can be adapted to determine the spatial and/or temporal distribution of energy-dependent reference values in accordance with the generated spectral computed tomography projection data such that for each generated spectral computed tomography projection data value, which corresponds to a certain position of a corresponding detection element of a detector used for generating the spectral computed tomography projection data and/or to a certain acquisition time, the determined spatial and/or temporal distribution of energy-dependent reference values provides a corresponding energy-dependent reference value. This spatial and/or temporal distribution of energy-dependent reference values may be used for correcting the spectral computed tomography projection data, which can lead to a further improved quality of a computed tomography image which may be reconstructed based on the corrected spectral computed tomography projection data.

In an embodiment the reference values generation device comprises a) different fluorescent elements for emitting fluorescent radiation when the polychromatic radiation impinges on the fluorescent elements, b) several non-energy-resolving reference detectors assigned to the several different fluorescent elements, in order detect the fluorescent radiation and generate fluorescence detection values based on the detected fluorescent radiation, and c) an energy-dependent reference values generation unit for generating the energy-dependent reference values based on the generated fluorescence detection values. Preferentially, the different fluorescent elements comprise K-edges at different energies within the spectrum of the polychromatic radiation provided by the radiation device. The fluorescent elements can therefore also be regarded as being K-edge elements. The energy-dependent reference values generation unit may be adapted to model a fluorescence detection value as an energy-integrated combination of a fluorescence yield $\omega_k$ of the respective fluorescent element, a linear absorption coefficient $\mu_k(E)$ for absorption by the photoeffect of the respective fluorescent element and the polychromatic radiation $\Phi(E)$ provided by the radiation device and to determine the polychromatic radiation $\Phi(E)$ as energy-dependent reference values based on the model, known fluorescence yields $\omega_k$, known absorption coefficients $\mu_k(E)$ and the generated fluorescence detection values. Thus, the energy-dependent reference values may be determined by using non-energy resolving reference detectors, which are generally technically less complex, easier to produce and hence less expensive than energy-resolving detectors. The fluorescent elements are preferentially arranged in a line in the direction of the polychromatic radiation provided by the radiation device, wherein the non-energy-resolving reference detectors are arranged to detect the fluorescent radiation in a detection direction which is transversal to the direction of the polychromatic radiation provided by the radiation device.

In an embodiment the reference values generation device comprises a) a non-energy-resolving detector for detecting the radiation, which has been provided by the radiation device and which has not traversed the examination zone, and for generating non-energy-depending detection values based on the detected radiation, and b) a reference values generation unit for generating the energy-dependent reference values based on the generated non-energy-depending detection values, a known energy-dependent number of photons, a known energy-dependent dead time of the spectral projection data generation device, a known energy-dependent average linear attenuation and a known material thickness. Also this allows for a generation of energy-dependent reference values by using a non-energy-resolving reference detector, which is generally technically less complex, easier to produce and hence less expensive than energy-resolving detectors. In this embodiment the spectral parameter providing unit is preferentially adapted to provide the energy-dependent reference values as the spectral parameters.

The energy-dependent number of photons, the energy-dependent dead time and the energy-dependent average linear attenuation are preferentially known from a previous calibration measurement, wherein the calibration measurement is preferentially performed for different thicknesses of a calibration material which is preferentially a water-like material.

Preferentially, the energy dependence relates to the assignment of the respective parameter to a respective energy bin. For instance, the energy-dependent number of photons, the energy-dependent dead time and the energy-dependent average linear attenuation are preferentially an energy-bin-dependent number of photons, an energy-bin-dependent dead time and an energy-bin-dependent average linear attenuation, respectively.

In another aspect of the present invention a spectral computed tomography system is presented, wherein the spectral computed tomography system comprises:

a system for generating spectral computed tomography projection data as defined in claim 1, and a reconstruction unit for reconstructing an image based on the generated spectral computed tomography projection data.

In a further aspect of the present invention a method for generating spectral computed tomography projection data is presented, wherein the method comprises:

providing polychromatic radiation for traversing an examination zone of the system by a radiation device, generating spectral computed tomography projection data based on the radiation after having traversed the examination zone by a spectral projection data generation device, generating energy-dependent reference values based on radiation, which has been generated by the radiation device and which has not traversed the examination zone, by a reference values generation device, and providing a spectral parameter being indicative of a spectral property of the radiation device based on the energy-dependent reference values by a spectral parameter providing unit.

In another aspect of the present invention a computer program for controlling a system for generating spectral computed tomography projection data as defined in claim 1 is presented, wherein the computer program comprises program code means for causing the system to carry out the steps of the method for generating spectral computed tomography projection data as defined in claim 14, when the computer program is run on a computer controlling the system.

It shall be understood that the system for generating spectral computed tomography projection data of claim 1, the spectral computed tomography system of claim 13, the method for generating spectral computed tomography projection data of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
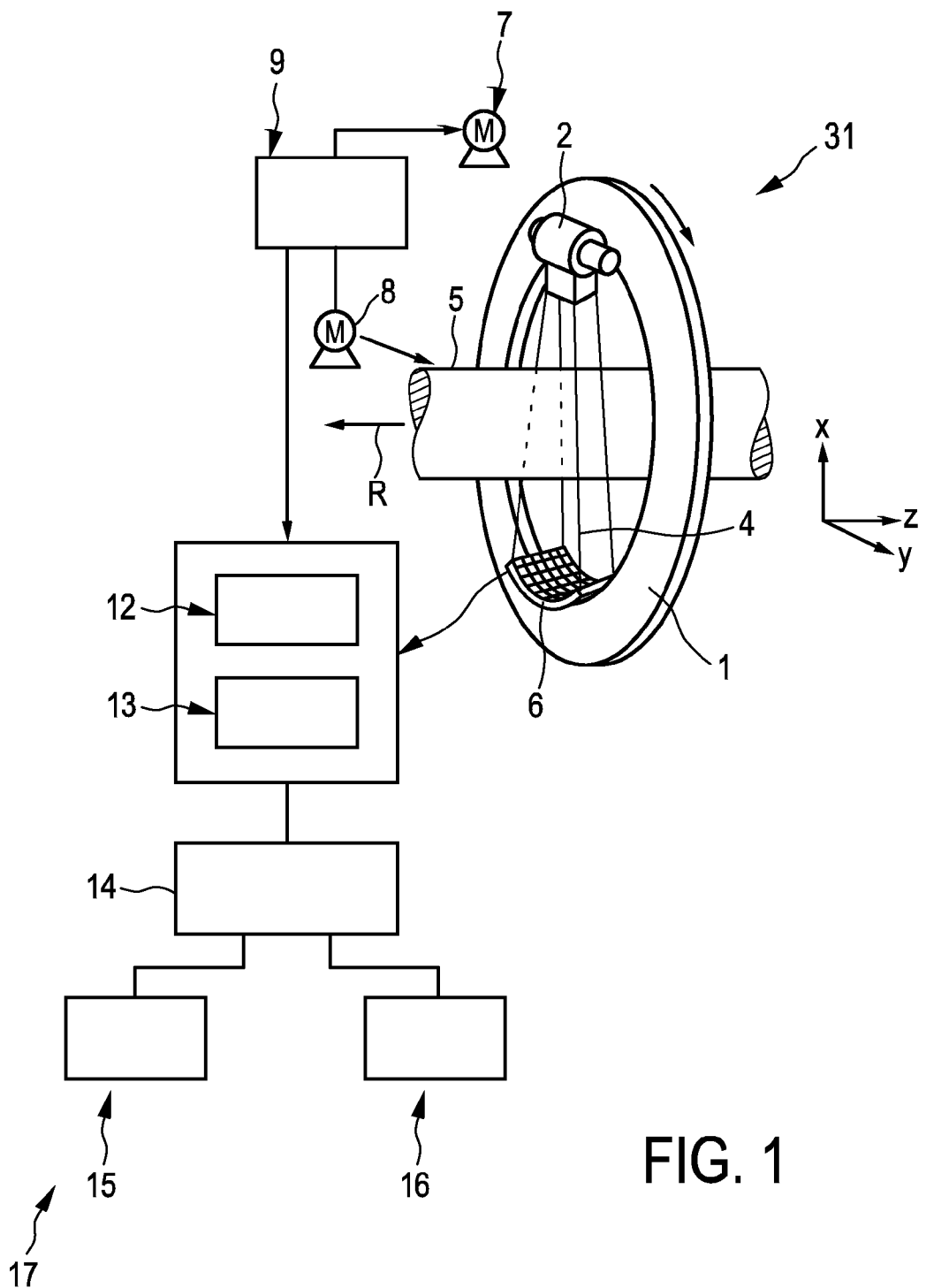
FIG. 1 shows schematically and exemplarily an embodiment of a spectral computed tomography system.

FIG. 1 shows schematically and exemplarily an embodiment of a spectral computed tomography system for generating an image of an object. The spectral computed tomography system 17 includes a support 1 which is capable of rotation about a rotational axis R which extends parallel to the z direction. A radiation device 2, which comprises an x-ray tube and which is adapted to provide polychromatic radiation 4 for traversing an examination zone 5 of the spectral computed tomography system 17, is mounted on the support 1. In this embodiment the radiation device 2 is adapted to provide a conical radiation beam 4 as the polychromatic radiation. In another embodiment, the radiation device 2 can be adapted to provide the polychromatic radiation with another beam shape, for instance, with a fan beam shape. The radiation 4 traverses an object (not shown) such as a patient in the examination zone 5, which is cylindrical in this embodiment. After having traversed the examination zone 5 the radiation beam 4 is incident on a spectral projection data generation device 6 which comprises a two-dimensional detection surface. The spectral projection data generation device 6 is mounted on the support 1.

The spectral computed tomography system 17 comprises two motors 7, 8. The support 1 is driven at a preferably constant but adjustable angular speed by the motor 7. The motor 8 is provided for displacing the object, for example, a patient, who is arranged on a table in the examination zone 5, parallel to the direction of the rotational axis R or the z-axis. The motors 7, 8 are controlled by a control unit 9, for instance, such that the radiation device 2 and the object within the examination zone 5 move relatively to each other along a helical trajectory. However, it is also possible that the object within the examination zone 5 is not moved, but that only the radiation device 2 is rotated, i.e. that the radiation device 2 moves along a circular trajectory relative to the object.

During the movement of the radiation device 2 relative to the object the spectral projection data generation device 6 generates spectral computed tomography projection data based on the radiation 4 incident on the detection surface of the spectral projection data generation device 6. Therefore, the radiation device 2, the elements for moving the radiation device 2 relative to the object, in particular, the motors 7, 8 and the support 1, and the spectral projection data generation device 6 can be regarded as being components of a system 31 for generating spectral computed tomography projection data.

The spectral computed tomography system 17, especially the system 31 for generating spectral computed tomography projection data, further comprises a reference value generation device for generating energy-dependent reference values based on radiation of the radiation device 2, which has not traversed the examination zone 5, a spectral parameter providing unit 12 for providing spectral parameters, which are indicative of the spectral properties of the radiation device 2, based on the energy-dependent reference values, and a correction unit 13 for correcting the generated spectral computed tomography projection data based on the determined spectral parameters. A reconstruction unit 14 reconstructs a computed tomography image based on the generated spectral computed tomography projection data by using known reconstruction algorithms. The reconstruction may be based on, for instance, a filtered back projection technique, an iterative reconstruction technique, a Radon inversion technique, et cetera. The reconstruction may include a decomposition of the spectral computed tomography projection data into different components, which may be related to different materials of the object within the examination zone 5 and/or to different physical effects, and a generation of one or more computed tomography images based on the decomposed spectral computed tomography projection data. For instance, a computed tomography image may be reconstructed, which is indicative of a single decomposed component only or of several of the decomposed components. The reconstructed computed tomography image may be shown on a display 16. Also the determined spectral parameters, which are indicative of the spectral properties of the radiation device 2, may be shown on the display 16. For decomposing the spectral computed tomography projection data into different components known decomposition algorithms can be used like the algorithm disclosed in "Experimental feasibility of multi-energy photon-counting K-edge imaging in pre-clinical computed tomography" by J. P. Schlomka et al., Physics in Medicine and Biology, volume 53, pages 4031 to 4047 (2008), which is herewith incorporated by reference.

The computed tomography system further comprises an input unit 15 like a computer mouse, a keyboard, a touchpad, et cetera, in order to allow a user to, for instance, input commands like start or stop commands and/or set parameters like acquisition and reconstruction parameters. The control unit 9 may also control the reference values generation device, the spectral parameter determination device 12, the correction unit 13 and/or the reconstruction unit 14.

The spectral projection data generation device 6 preferentially comprises a photon-counting detector for generating the spectral computed tomography projection data, wherein the photon-counting detector preferentially comprises a direct-conversion material like Cd(Zn)Te. Such a photon-counting detector is known, for instance, from "ChromAIX: Fast photon-counting ASIC for Spectral Computed Tomography" by R. Steadman, et al., Nuclear Instruments and Methods in Physics Research Section A: Accelerators, Spectrometers, Detectors and Associated Equipment, volume 648, supplement 1, pages S211 to S215 (2011), which is herewith incorporated by reference.

Figure 2:
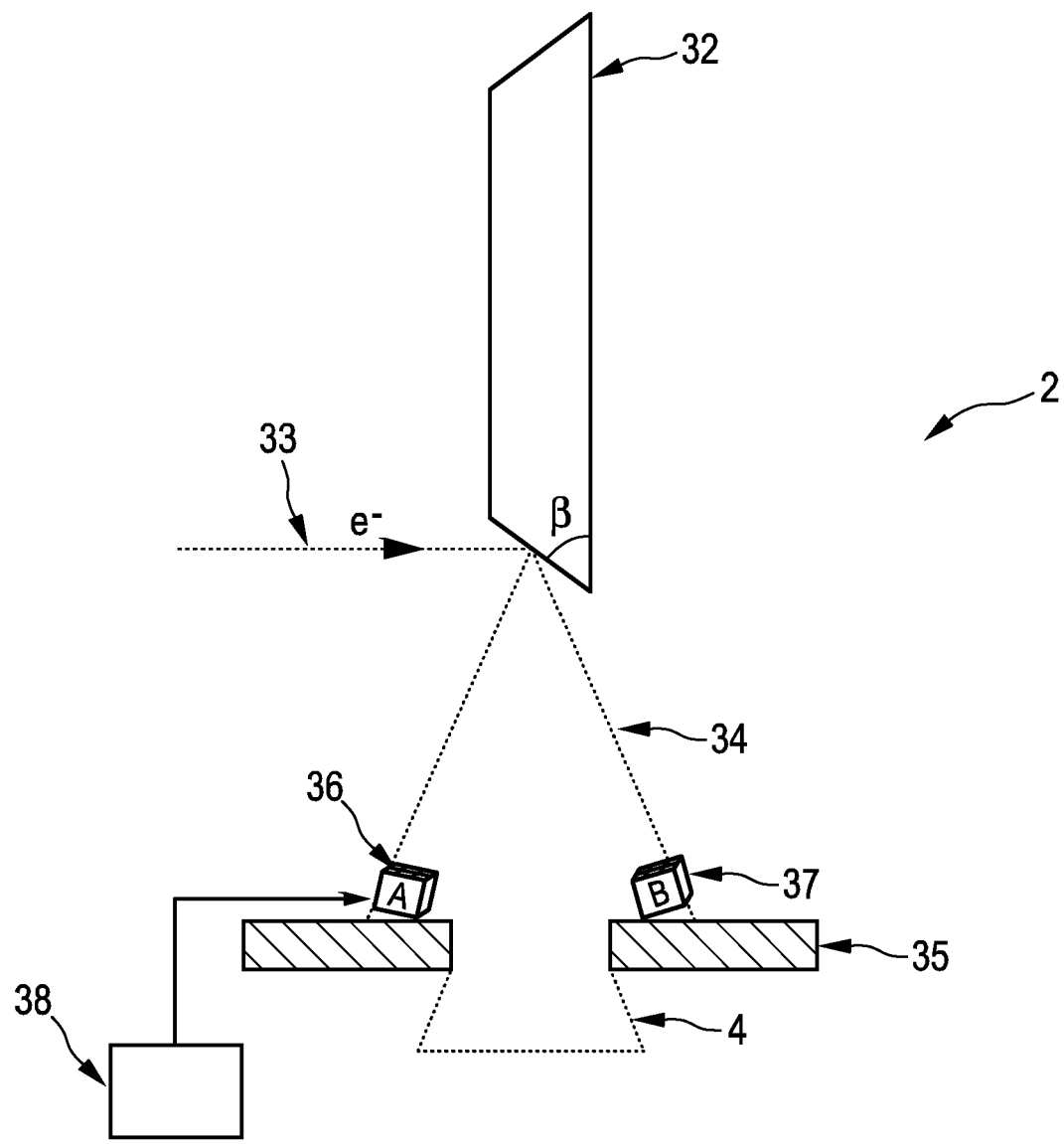
FIG. 2 shows schematically and exemplarily an embodiment of a radiation device of the spectral computed tomography system comprising an embodiment of a reference values generation device.

FIG. 2 exemplarily and schematically illustrates components of an embodiment of the radiation device 2 and of the reference values generation device in more detail. In this embodiment the radiation device 2 comprises as a radiation source with an anode 32, on which an electron beam 33 impinges, in order to generate polychromatic radiation 34. The generated polychromatic radiation 34 is collimated by a collimator 35, in order to generate the conical radiation beam 4. Energy-resolving reference detectors 36, 37 of the reference values generation device are arranged between the collimator 35 and the radiation source, i.e. the anode 32, such that the energy-resolving reference detectors 36, 37 do not disturb the conical radiation beam 4 and detect parts of the polychromatic radiation 34, which do not pass the collimator 35. They may be arranged on surfaces of the collimator 35, which are directed towards the anode 32. The energy-resolving detectors 36, 37 are preferentially of the same type as the detector of the spectral projection data generation device 6, i.e. preferentially also the energy-resolving reference detectors 36, 37 are photon-counting detectors.

In other embodiments the reference detectors can be arranged at other positions. In particular, the reference detectors can be integrated in a collimator box together with a bowtie filter and/or a spectral filter, wherein the reference detectors can be arranged before and/or behind the filters. Moreover, the reference detectors may be integrated in a housing of the x-ray tube, especially next to or in an x-ray window of the housing. Furthermore, the reference detectors may be mounted on the rotating support supporting the radiation device 2 with the x-ray tube and the spectral projection data generation device 6, particularly next to the spectral projection data generation device 6 such that the reference detectors can detect radiation which has not been blocked by the object to be imaged, i.e. which has not traversed the examination zone 5. The reference detectors may also be mounted on a fixture that might be attached to the radiation device 2, especially the x-ray tube and/or the collimator box, the rotating support et cetera, in order to detect radiation which has not traversed the examination zone 5.

The energy-resolving reference detectors 36, 37 are arranged at different positions, especially at opposing sides of the collimator opening, and each energy-resolving reference detector 36, 37 comprises an array of detection pixels, wherein different detection pixels are of course located at different positions. The energy-resolving reference detectors 36, 37 can therefore generate energy-dependent reference values, which correspond to different positions. Moreover, the energy-resolving reference detectors 36, 37 can generate energy-dependent reference values, which correspond to different times, i.e. different acquisition times.

The reference values generation device further comprises a calculation unit 38 for calculating as the spectral parameter a spatial and temporal distribution of energy-dependent reference values based on the generated energy-dependent reference values. In particular, by extrapolation and/or interpolation energy-dependent reference values are calculated for positions and/or times, for which the energy-resolving reference detectors 36, 37 have not generated reference values, in order to calculate the spatial and temporal distribution of energy-dependent reference values. Preferentially, the calculation unit 38 is adapted to calculate reference values for positions within the opening of the collimator 35 and/or for times at which the spectral computed tomography projection data have been acquired.

The reference values generated by the energy-resolving reference detector 36 may be denoted by $I^A(E_i, x_j^A, y_K^A, t_l)$, wherein $E_i$ denotes the different energies, for which reference values are generated, $x_j^A$ denotes different x positions of detection pixels of the reference detector 36, $y_k^A$ denotes different y positions of detection pixels of the reference detector 36 and $t_l$ denotes different times at which the reference values have been generated by the reference detector 36. The reference values generated by the reference detector 37 may be denoted by $I^B(E_i, x_m^B, y_n^B, t_l)$, wherein $x_m^B$ denotes different x positions of the detection elements of the reference detector 37 and $y_n^B$ denotes different y positions of the detection elements of the reference detector 37. The calculated reference values, which may be calculated by interpolation and/or extrapolation, preferentially correspond to detection elements of the spectral projection data generation device 6, wherein these calculated reference values may be denoted by $I^C(E_i, x_o^C, y_p^C, t_l)$, wherein $x_o^C$ denotes different x positions of the detection elements of the spectral projection data generation device 6 and $y_p^C$ denotes different y positions of the detection elements of the spectral projection data generation device 6. The spectral parameter providing unit 12 can be adapted to provide the measured reference values $I^A(E_i, x_j^A, y_K^A, t_l)$ and $I^B(E_i, x_m^B, y_n^B, t_l)$ and/or the calculated reference values $I^C(E_i, x_o^C, y_p^C, t_l)$ as the spectral parameter, because these reference values are of course directly indicative of the spectral properties of the radiation device 2. The correction unit 13 can be adapted to correct the spectral computed tomography projection data based on the calculated reference values $I^C(E_i, x_o^C, y_p^C, t_l)$. The spectral computed tomography projection data can be corrected, for instance, by dividing the respective spectral computed tomography projection data value, which has been acquired for a certain energy, position on the detection surface and time, by the corresponding reference value $I^C(E_i, x_o^C, y_p^C, t_l)$, especially by multiplying the respective spectral computed tomography projection data value by the corresponding quotient $I_0^C(E_i, x_o^C, y_p^C, t_0)/I^C(E_i, x_o^C, y_p^C, t_l)$, wherein $I_0^C(E_i, x_o^C, y_p^C, t_0)$ denotes the calculated reference value for a reference time $t_0$.

The calculated reference values give information on the spatial distribution of the spectrum with respect to the reference detectors but also in an extrapolated and/or interpolated way with respect to the positions of the main detector, i.e. the spectral projection data generation device 6. Processing of the data from the reference detectors leads to the information $I^C(E_i, x_o^C, y_p^C, t_l)$ which can be used to analyze the position dependent spectrum information, spectrum changes over time and/or spectrum changes over local positions that might depend on the actual operation mode of the x-ray tube including changes of the acceleration voltage, the emission current, the focusing and beam shaping and the position of the focal spot. Differences and also time dependent processing may be used for history dependent processing but can also be used for future prediction of the performance. In particular, the reference values can be saved and used for developing a model of spectral degradation over time, for instance by using multivariate regression. In an embodiment this model is used for predicting the spectral status of future systems and/or for, for instance, predictive maintenance.

The spectral parameter providing unit 12 can also be adapted to calculate other entities, which are indicative of the spectral properties of the radiation device 2, based on the measured reference values $I^A(E_i, x_j^A, y_K^A, t_l)$ and/or $I^B(E_i, x_m^B, y_n^B, t_l)$ and/or the calculated reference values $I^C(E_i, x_o^C, y_p^C, t_l)$. For instance, the difference between reference values measured by the reference detector 36 and reference values measured by the reference detector 37 can be determined, wherein this difference may be an average difference, i.e. an average value may be determined for the reference detector 36, a further average value may be determined for the reference detector 37, and these average values may be subtracted from each other. The average values may be temporal and/or spatial averages and may depend on the energy such that an energy-dependent average difference can be calculated. It is also possible that the spectral parameter providing unit 12 determines for each detection element of a same reference detector 36, 37 a difference between reference values detected at different times, wherein these differences are provided as the spectral parameter.

There are several processes that can lead to spectral changes of a radiation device comprising an x-ray tube. For example, a focal track on an anode may show an increasing surface roughness with time due to wear and erosion caused by the high-energy electron beam. The roughness may be inhomogeneous on the anode surface, because the electron beam on the anode, i.e. the focal spot, may be modified, which may lead to inhomogeneous wear and erosion. In an embodiment, the x-ray tube may be a dual-focal spot (DFS) x-ray tube, wherein repeatedly the focal spot is displaced on the anode such that the radiation emanates from two or more different locations, and/or the x-ray tube may be adapted to use different focal spot sizes. An increased surface roughness will lead to a hardening of the radiation, because lower energies are more strongly attenuated in the roughened anode than higher energies and this effect increases with increasing roughness. Furthermore, spectral changes can result from different impingent angles of the electron beam onto the anode surface at different focal spot locations, which may be used in case of DFS, and from unintentional focal spot movements due to the anode rotation field.

Figure 3:
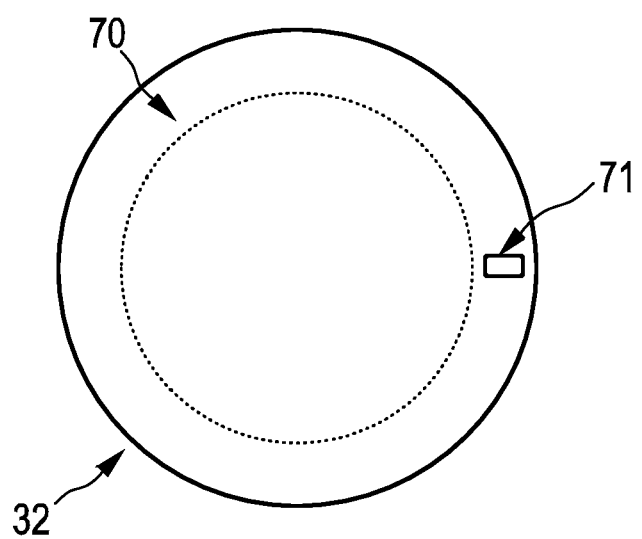
FIG. 3 shows schematically and exemplarily a top view of an embodiment of an anode of a radiation device.
Figure 4:
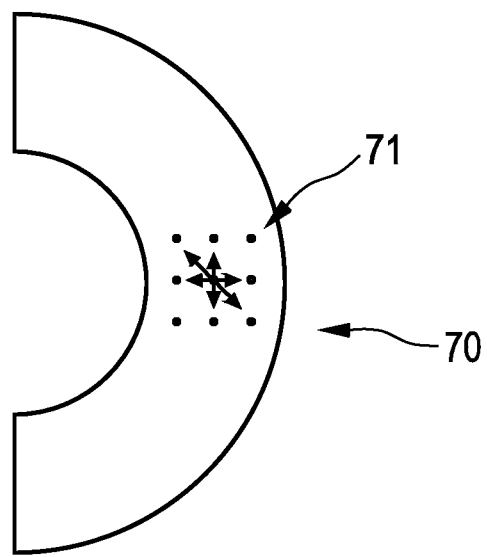
FIG. 4 illustrates schematically and exemplarily different focal spots on an angulated surface of an embodiment of an anode of a radiation device.
Figure 5:
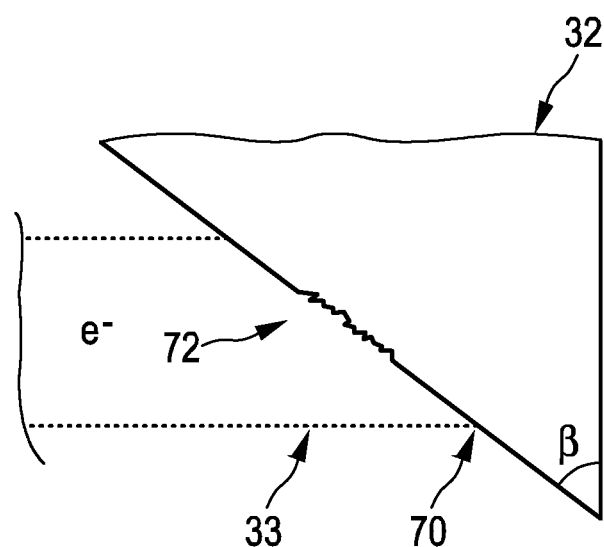
FIG. 5 shows schematically and exemplarily a sectional view of a part of an angulated surface of an embodiment of an anode and an electron beam impinging on this part of the angulated surface.

FIG. 3 shows schematically and exemplarily a top view on the anode 32 comprising an angulated surface 70 with an angulation angle β which is indicated in FIGS. 2 and 5 and which may be about, for instance, 7 degrees. Moreover, in FIG. 3 a focal spot region 71 is illustrated, which is shown in more detail in FIG. 4. FIG. 4 illustrates a top view on a part of the angulated surface 70 of the anode 32, wherein in the focal spot region 71 the focal spot may be repeatedly moved to different locations on the angulated surface 70, especially if the x-ray tube is a DFS tube. FIG. 5 shows schematically and exemplarily a sectional view through a part of the anode 32, wherein a roughness 72 is schematically illustrated on the angulated surface 70, which leads to an increased heel effect.

The spectrum of the polychromatic radiation of the radiation device can also vary with the position along the fan angle, i.e. the angle to the anode surface 70, because the self absorption of the radiation along this direction, i.e. the heel effect, has a larger influence on the lower energy part of the spectrum of the polychromatic radiation provided by the radiation device and a smaller influence on the higher energy part of the spectrum. Due to the heel effect the x-ray intensity also decreases with decreasing angle between a respective x-ray and the anode surface 70. The influence of the heel effect increases with increasing anode surface roughness during tube lifetime. For the extrapolation of these effects it may be helpful to have a detailed understanding of the angular distribution of the spectrum of the polychromatic radiation provided by the radiation device 2.

The computed tomography system, especially the system for generating spectral computed tomography projection data, described above with reference to FIGS. 1 and 2 is preferentially adapted to determine variations in the tube output spectrum over time and position. For determining the tube output spectrum over time and position the two reference detectors 36, 37 comprising several detection elements, i.e. detection pixels, are used. However, in another embodiment it is also possible that only one energy-resolving reference detector having several detection elements, i.e. detection pixels, is used or that two or more energy-resolving reference detectors are used, wherein each energy-resolving reference detector comprises a single detection element only. Thus, at least two detection pixels can be used as energy-resolving detectors for generating the reference detection values, wherein the at least two detection pixels of course are arranged at different locations. The reference detection values can be used to account for, for instance, the heel effect which will increase during tube lifetime, i.e. the intensity drop with decreasing angle between the respective x-ray beam and the anode surface will get more and more pronounced during tube lifetime. Also spectral hardening will increase with time and with decreasing angle between the respective x-ray beam and the anode surface.

The spectral computed tomography system is preferentially adapted to estimate spectral changes over time and over position and use these estimated changes for calibration during image reconstruction, i.e. for correcting the generated spectral computed tomography projection data before using the same for reconstructing the image. This estimation is preferentially based on two or more reference detectors arranged between the anode of an x-ray tube and a collimator, wherein at least one of these reference detectors provides energy-dependent reference values. The reference detectors are preferentially located at fixed places in the spectral computed tomography system and preferentially comprise a filter element for filtering the radiation to be detected by the reference detectors before impinging on a detection surface of the reference detectors, in order to ensure that the radiation to be detected is within an intensity range detectable by the reference detectors. The correction unit can be adapted to correct the spectral computed tomography projection data frame-by-frame. In particular, for each frame, i.e. for the acquisition time at which the respective frame has been acquired, a spatial distribution of reference values can be estimated and used for correcting the respective frame. The reference values can also be stored, in order to perform, for instance, a histogram or multivariate regression based analysis which can be used for a trend analysis of anode aging as well as focal point, spectral, and intensity degradation monitoring and prediction.

The energy and spatially resolved reference values, and/or correction factors like $I^C(E_i,x_o^C,y_p^C,t_0)/I^C(E_i,x_o^C,y_p^C,t_l)$ computed from these, can be stored and analyzed for several imaging systems. The analysis methods can include but are not limited to machine learning algorithms, support vector machines, neural networks, multivariate regression and histogram analysis. In this way, a model of spectral, intensity and/or focal spot size degradation can be built. Such a model can be used in the monitoring of x-ray sources or imaging systems in order to provide degradation prediction, which is useful for pro-active services and, for instance, for minimizing unplanned down times.

The energy-dependent reference values generated by the reference detectors between the collimator and the anode of the x-ray tube are preferentially not only used for correcting current spectral computed tomography projection data, but also for providing system status information. The data processing used for processing the energy-dependent reference values comprises preferentially a split, in order to use the energy-dependent reference values for these two different purposes.

The technique for monitoring the spectral properties of the radiation device can be used, for instance, for x-ray tubes in medical imaging systems, material analysis and quality assurance systems, as well as luggage scanning systems and other security systems.

Figure 6:
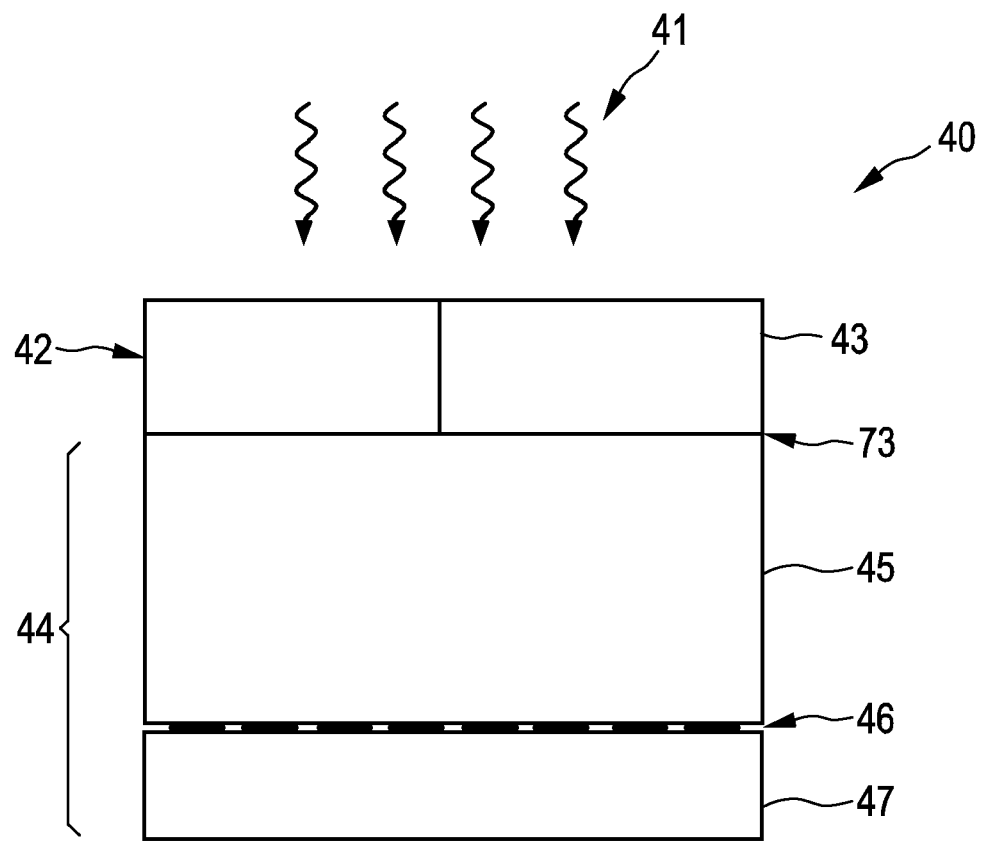
FIGS. 6 to 8 show schematically and exemplarily further embodiments of a reference values generation device.

FIG. 6 schematically and exemplarily illustrates a further embodiment of a reference value generation device 40, which may be arranged between the collimator and the anode of the x-ray tube of the radiation device similar to the arrangement of the reference detectors illustrated in FIG. 2, or at another location where radiation of the radiation device 2 can be detected, which has not traversed the examination zone 5.

The reference values generation device 40 comprises two K-edge elements 42, 43 having K-edges at different energies within the spectrum of the polychromatic radiation 41. The K-edge elements 42, 43 are arranged on a detection surface of an energy-resolving reference detector 44 such that the radiation 41 is filtered by the K-edge elements 42, 43 before being detected by the reference detector 44. The reference detector 44 comprises a direct conversion crystal like Cd(Zn)Te between a cathode 73 and a pixilated anode 46. The pixilated anode 46 is connected to an energy-resolving photon-counting application-specific integrated circuit (ASIC) 47, in order to generate energy-dependent reference values. In the example shown in FIG. 6 the K-edge elements 42, 43 are arranged side-by-side on the detection surface of the reference detector 44. Moreover, in this example the K-edge element 42 is iodine and the K-edge element 43 is gadolinium. The two K-edge elements 42, 43 can be placed at the same angle from the normal of the slanted anode 32 of the x-ray tube, in order to not confound the result with a position sensitivity due to an increasing heel effect.

In FIG. 6 it is schematically illustrated that the two K-edge elements 42, 43 are placed on two different areas on the reference detector 44. However, the K-edge elements can also be arranged in another way on the reference detector 44. For instance, as schematically and exemplarily illustrated in FIG. 7, two K-edge elements 52, 53 may be arranged on the detection surface of the reference detector 44 on top of each other, i.e. they may form a stack arranged on the detection surface of the reference detector 44 of a reference values generation device 50. In the example shown in FIG. 7 the K-edge element 52 might be gadolinium and the K-edge element 53 might be iodine. The reference value generation device may also comprise more than two K-edge elements, especially three K-edge elements. Moreover, the different K-edge elements may be arranged side-by-side and on top of each other as schematically and exemplarily illustrated in FIG. 8.

Figure 8:
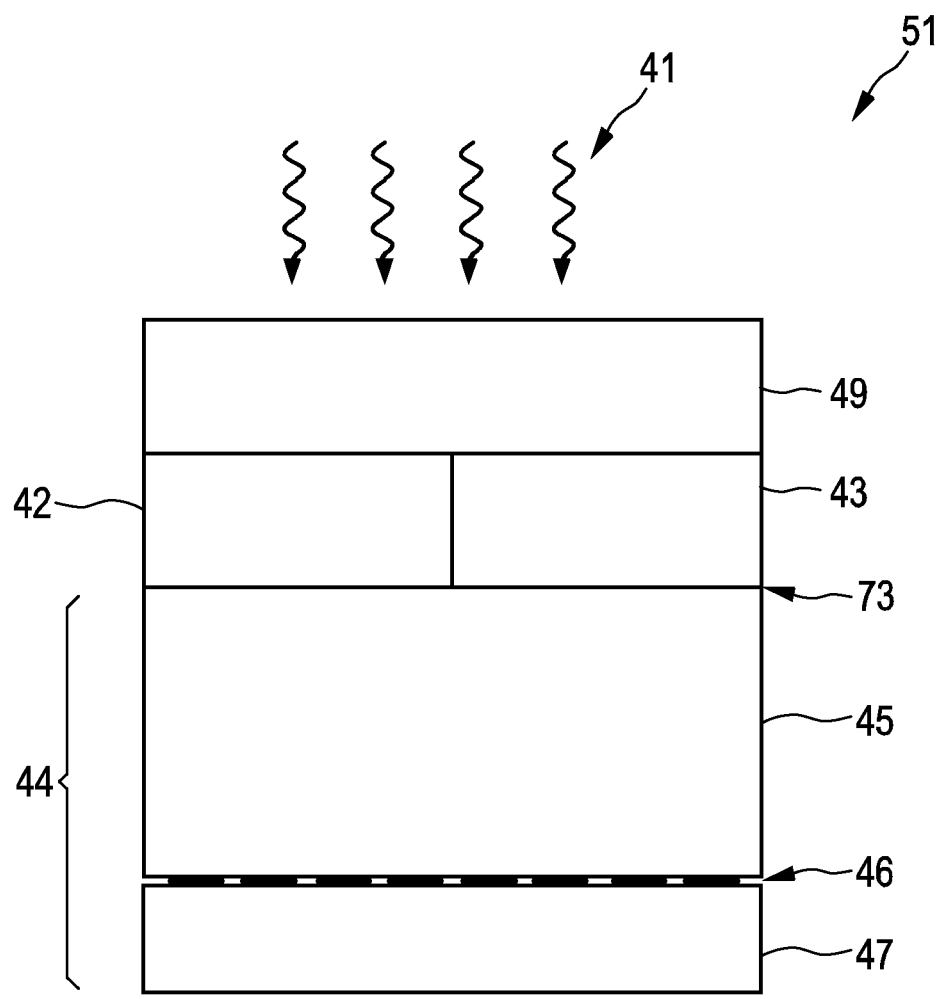

The reference values generation device 51 schematically and exemplarily illustrated in FIG. 8 comprises three K-edge elements 42, 43, 49, wherein two K-edge elements 42, 43 are arranged side-by-side on the detection surface of the reference detector 44 and a third K-edge element 49 is arranged on top of both, the first and second K-edge elements 42, 43. In this example the first K-edge element 42 may be iodine, the second K-edge element 43 may be gadolinium and the third K-edge element 49 may be lead.

The spectral parameter providing unit 12 can be adapted to a) determine the spectral parameter based on the spectral reference values at the energies, at which the K-edges are present, and/or b) calculate different summed values by summarizing spectral reference values for energies being smaller than the lowest energy, at which a K-edge is present, and/or for energies between energies, at which different K-edges are present, and/or for energies being larger than the largest energy, at which a K-edge is present, and to determine the spectral parameter based on the summed values. For instance, the spectral parameter providing unit 12 can be adapted to determine the spectral parameter based on ratios of spectral reference values at different energies, at which the K-edges are present. Moreover, the spectral parameter providing unit 12 can be adapted to determine the spectral parameter based on ratios of summed values. In particular, the ratios of the summed values and/or the ratios of the spectral reference values at different energies, at which the K-edges are present, can be determined for different times and the ratios determined for the different times can be compared, in order to determine a spectral parameter which is indicative of a change of the spectrum of the polychromatic radiation over time.

In order to decompose the spectral computed tomography projection data and use the decomposed spectral computed tomography projection data for reconstructing a computed tomography image, the spectrum of the polychromatic radiation provided by the radiation device and the spectral response of the detection system of the spectral projection data generation device need to be known. As already mentioned above, during tube lifetime the impinging electron beam can erode the focal track on the anode, causing increased surface roughness and small tracks. This can lead to a reduction of the tube output dose over time and also to spectrum hardening and an increased heel effect due to an increased self absorption at lower energies in the rough anode. The spectral computed tomography system is therefore preferentially adapted to assess the spectral changes, in order to correct the assumed spectral response of the system. By continuously monitoring the spectral output of the tube, measures can be taken to compensate for changes of the nominal spectral output of the tube and to thereby avoid image artifacts caused by these changes, especially by a hardening of the spectrum, over time. In order to obtain a quantifiable measure of the spectral tube degradation, K-edge filters, i.e. the above-mentioned K-edge elements, can be placed on an energy-resolving reference detector. The use of filters also affects the impinging spectrum on the reference detector. However, the analysis of the K-edge feature allows neglecting the effect of the filters on the impinging spectrum, especially the hardening effect, by restricting the analysis to an evaluation of relative differences or ratios of two or more K-edges situated at different energies, wherein preferentially at least two different materials are used for the K-edge elements, wherein a first material has a lower energy K-edge position and a second material has a higher energy K-edge position.

Figure 9:
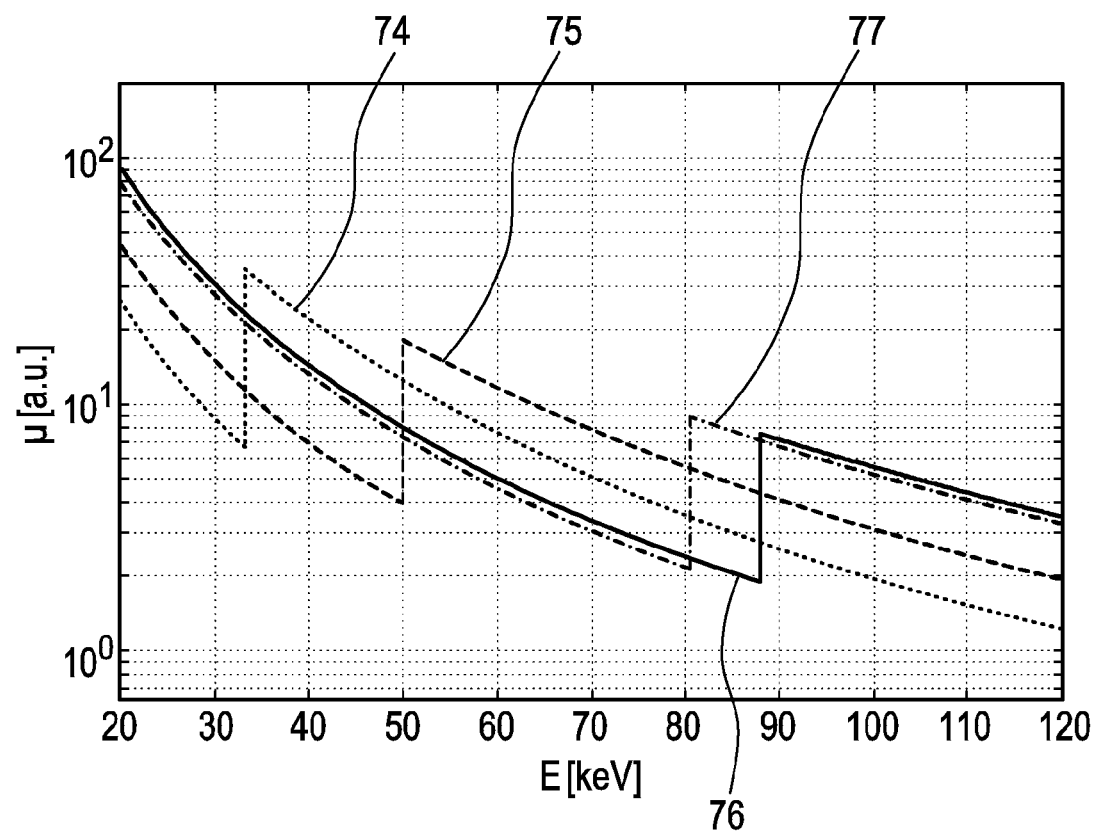
FIG. 9 illustrates schematically and exemplarily the attenuation of different materials having K-edges at different energies.

Thus, the spectral footprint of K-attenuation/edges caused by materials exhibiting a K-edge discontinuity within the relevant energy range for computed tomography applications, which might be from about 25 keV to 160 keV, may be used. The purpose of these materials is not only to reduce the flux, but rather to enable detecting and quantifying the K-edges in the resulting detected spectrum. FIG. 9 schematically and exemplarily shows the attenuation coefficient $\mu$ in arbitrary units depending on the energy E in keV for different materials having a K-edge in the relevant spectral range. In FIG. 9 the line 74 indicates the attenuation coefficients of iodine having a K-edge at 33.2 keV, the line 75 indicates attenuation coefficients of gadolinium having a K-edge at 50.2 keV, the line 76 indicates the attenuation coefficients of lead having a K-edge at 88.0 keV and the line 77 indicates the attenuation coefficients of gold having a K-edge at 80.7 keV.

The energy-resolving reference detector can quantify the K-edge characteristics of the materials placed on the detection surface of the energy-resolving reference detector. In order to assess the tube spectral degradation, the spectral parameter providing unit 12 can be adapted to continuously monitor the K-edge discontinuities present in the energy-dependent reference values generated by the reference values generation device. A tube exhibiting a hardened spectrum due to, for instance, anode degradation will cause the K-edge step of, for instance, iodine to become smaller with respect to the K-edge step of, for instance, gadolinium, which is situated at higher energies. The relative difference of two or more K-edge steps can therefore be evaluated and the evaluation result can be used as a spectral parameter giving an indication of the spectral degradation of the tube. Since in this example only the relative change of the ratios among K-edge discontinuities is considered, the spectral hardening caused by the K-edge filters is irrelevant.

The K-edge elements on the detection surface of the energy-resolving reference detector preferentially cover one or more detection elements, i.e. detection pixels, of the energy-resolving reference detector. The thickness of the K-edge elements is preferentially selected such that the photon rate reaching the detection surface of the energy-resolving reference detector is sufficiently high for providing good statistics but not too high, in order to not saturate the energy-resolving reference detector. The K-edge elements can be arranged on the detection surface of the energy-resolving reference detector as described above with reference to FIGS. 6 to 8 or they can be arranged in another way. In particular, a plurality of K-edge materials can be used, wherein two, three or more K-edge materials can be arranged on the detection surface of the energy-resolving reference detector, wherein the arrangement of these K-edge materials on the detection surface may be as described above with reference to FIGS. 6 to 8 or they may be arranged in another way.

The generated reference values may not only be used to assess the spectral degradation of the tube over lifetime, but also for providing a reference signal for the generation of the spectral computed tomography projection data in terms of the realtime flux of the radiation provided by the radiation device. This realtime flux can be used by the correction unit for correcting the generated spectral computed tomography projection data accordingly. In the following spectral parameters will exemplarily be described, which may be determined by the spectral parameter providing unit 12, in order to quantitatively assess the degradation of the spectral quality of the tube.

Figure 7:
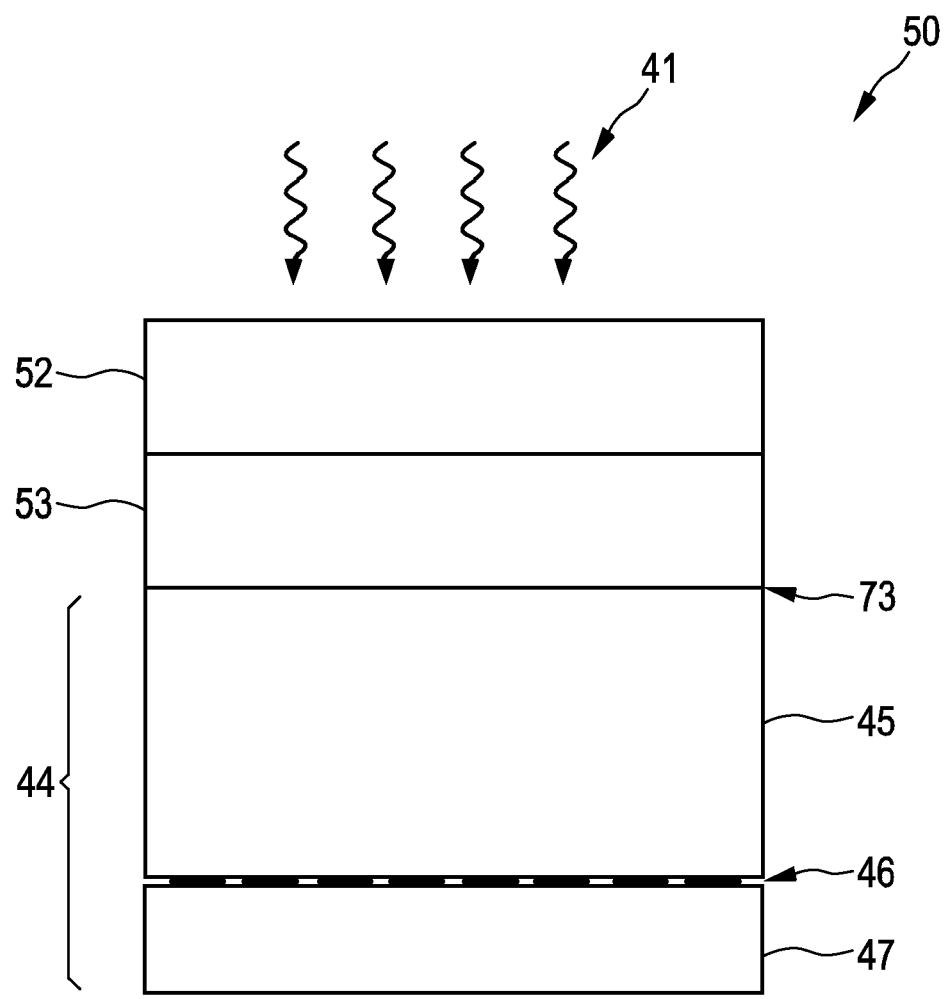
Figure 10:
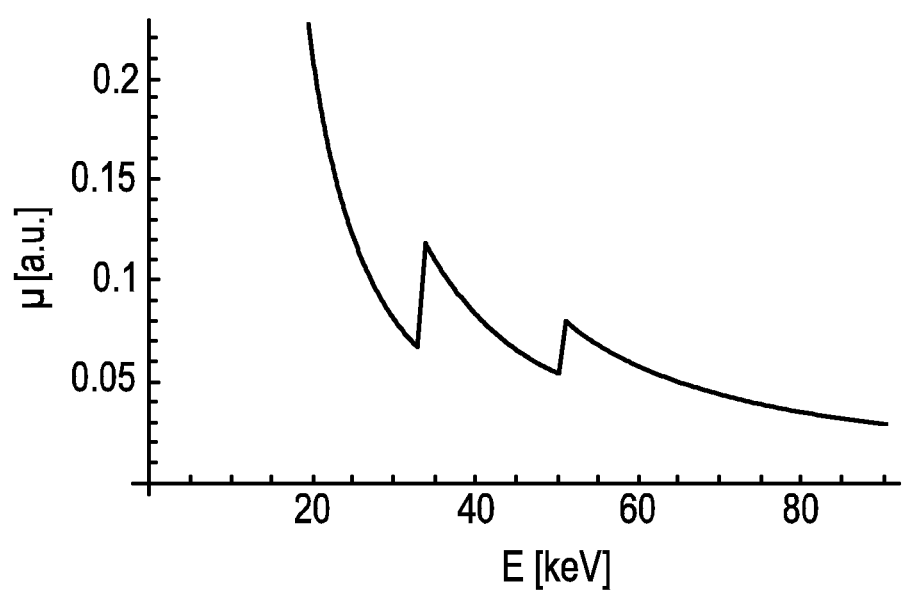
FIG. 10 illustrates schematically and exemplarily the attenuation of a combination of two different K-edge elements having K-edges at different energies.

FIG. 10 shows a line indicating the dependence of the attenuation coefficient $\mu$ for a filter combination of iodine and gadolinium for one and the same beam, i.e. with the corresponding K-edge elements on top of each other, for instance, as schematically and exemplarily illustrated in FIG. 7. The hardening of the beam due to aging influences the ratio of power detected in the spectrum by the energy-resolving reference detector, i.e. influences the ratio of the corresponding generated energy-dependent reference values, above and below the K-edge of iodine and gadolinium, respectively. The spectral parameter providing unit 12 can be adapted to determine the sum of counts, i.e. reference values, registered with energies up to the K-edge of iodine (B1), the sum of counts registered with energies between the K-edges of iodine and gadolinium (B2) and the sum of counts registered with energies above the K-edge of gadolinium (B3). The spectral parameter providing unit may be further adapted to calculate the ratio B1/B2, which is indicative of beam hardening in the low energy regime of the spectrum, and the ratio B2/B3, which is indicative of the beam hardening in the intermediate energy regime of the spectrum, as spectral parameters being indicative of the spectral properties of the radiation device. These ratios can be compared with respective ratios at delivery. In case the above ratios deviate by a predefined value from nominal ratios at delivery, the tube quality might be insufficient to guarantee adequate spectral performance. In this case counter measures may be taken by means of processing or tube replacement. The same result can be obtained by forcing the reference detector to provide a spectrum resulting from a threshold scan, i.e. energy scan. This can be performed at regular intervals to evaluate the drop in counts around the K-edge feature, i.e. with a threshold scan a small energy window can be used to obtain the necessary information.

When performing a threshold scan one or more thresholds can be incremented in discrete steps. For instance, a single threshold can be subsequently increased (or decreased) to register the number of detected counts at every single position. The result of such a scan is an accumulated spectrum, i.e., after differentiation the actual spectrum resolved by the detector can be obtained. Moreover, alternatively two or more thresholds may be used. Increasing both thresholds simultaneously results in a differentiated spectrum of better statistical quality, i.e. because both thresholds "see" the same noise, correlated noise is effectively eliminated.

Using the K-edge elements has the advantage that the ratios like the ratios B1/B2 and B2/B3 can be relatively large and detectable with a relatively high signal-to-noise ratio. The energy-dependent reference values can be logged locally or remotely and used as a measure of wear and to analyze the impact of the usage of the tube onto its spectral performance/degradation in realtime or, for instance, at certain time intervals. Spectral degradation above a certain predefined threshold value may be communicated to a service organization and/or a customer and used to trigger, for instance, service scheduling and pro-active shipping of replacement parts. The spectral computed tomography system can therefore provide an early detection of tube failure related to, for instance, anode and dose degradation.

Figure 11:
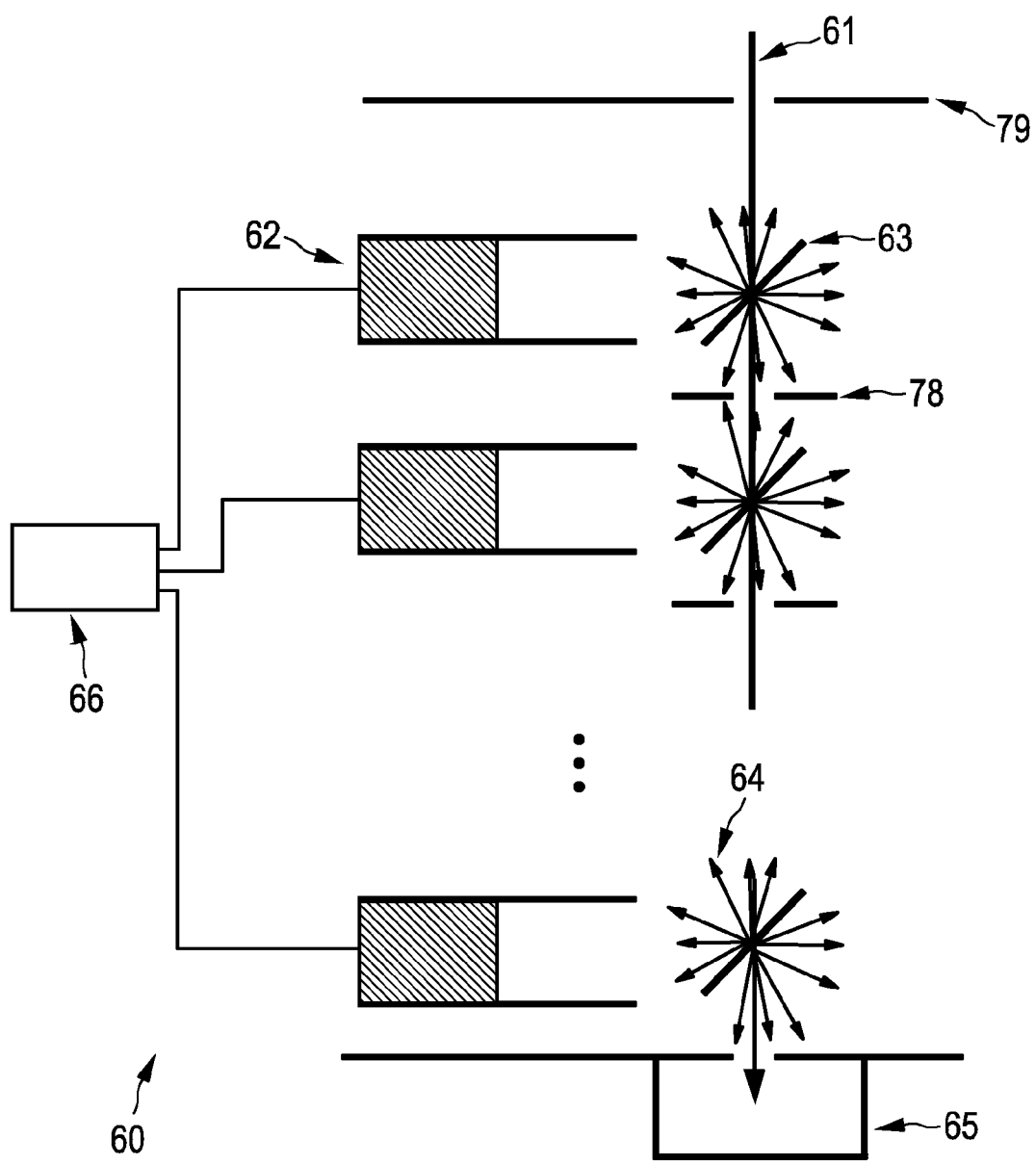
FIG. 11 shows schematically and exemplarily a further embodiment of a reference values generation device.

In a further embodiment the spectral computed tomography system 17 may comprise a reference values generation device 60 as schematically and exemplarily illustrated in FIG. 11. In particular, the reference values generation device 60 may comprise different fluorescent elements 63 for emitting fluorescent radiation 64 when a polychromatic radiation beam 61, which has been generated by using a collimator 79 for collimating the polychromatic radiation, impinges on the fluorescent elements 63. The reference values generation device 60 further comprises several non-energy-resolving reference detectors 62 assigned to the several different fluorescent elements 63, in order to detect the fluorescent radiation 64 and to generate fluorescence detection values based on the detected fluorescent radiation 64.

The different fluorescent elements 63 comprise K-edges at energies within the spectrum of the polychromatic radiation provided by the radiation device 2. The fluorescent elements 63 can therefore also be regarded as being K-edge elements. The fluorescent elements 63 are arranged in a line in the direction of the polychromatic beam 61, wherein the non-energy-resolving reference detectors 62 are arranged such that they detect the fluorescent radiation 64 in a detection direction being transversal to the direction of the polychromatic beam 61. The fluorescent elements 63 are arranged along the radiation 61 provided by the radiation device 2 such that the fluorescent element 63 with the lowest K-edge energy is first radiated by the beam 61, followed by the one with the second lowest K-edge energy and so forth. After the beam 61 has passed the last fluorescent element 63, it is blocked by a beam blocker 65. The reference values generation device 60 can comprise further collimators 78 and/or beam blockers at various positions, in order to maximize the fluorescence signal while reducing the amount of non-fluorescent radiation reaching the non-energy-resolving reference detectors 62. In order to optimize the effective primary flux at the individual fluorescent element 63, subsequent fluorescent elements 63 may comprise holes of equal or different cross sections. In particular, the cross sections of the holes may decrease downstream the incoming beam 61. In an embodiment the holes in the different fluorescent elements may have an offset to each other in a direction which is transversal to the direction of the beam 61, or subsequent pairs of non-energy-resolving reference detectors and fluorescent elements may be laterally displaced to each other, especially in the drawing plane shown in FIG. 11 or out of the drawing plane.

Thus, the reference values generation device therefore preferentially comprises an array of integrating, i.e. non-energy-resolving, reference detectors, which are preferentially scintillator based, in combination with an array of fluorescent elements, which may also be regarded as being fluorescent targets. The fluorescence output of each fluorescent element is detected by individual non-energy-resolving reference detectors, in order to analyze the spectral distribution of the primary photon flux provided by the radiation device 2.

Figure 12:
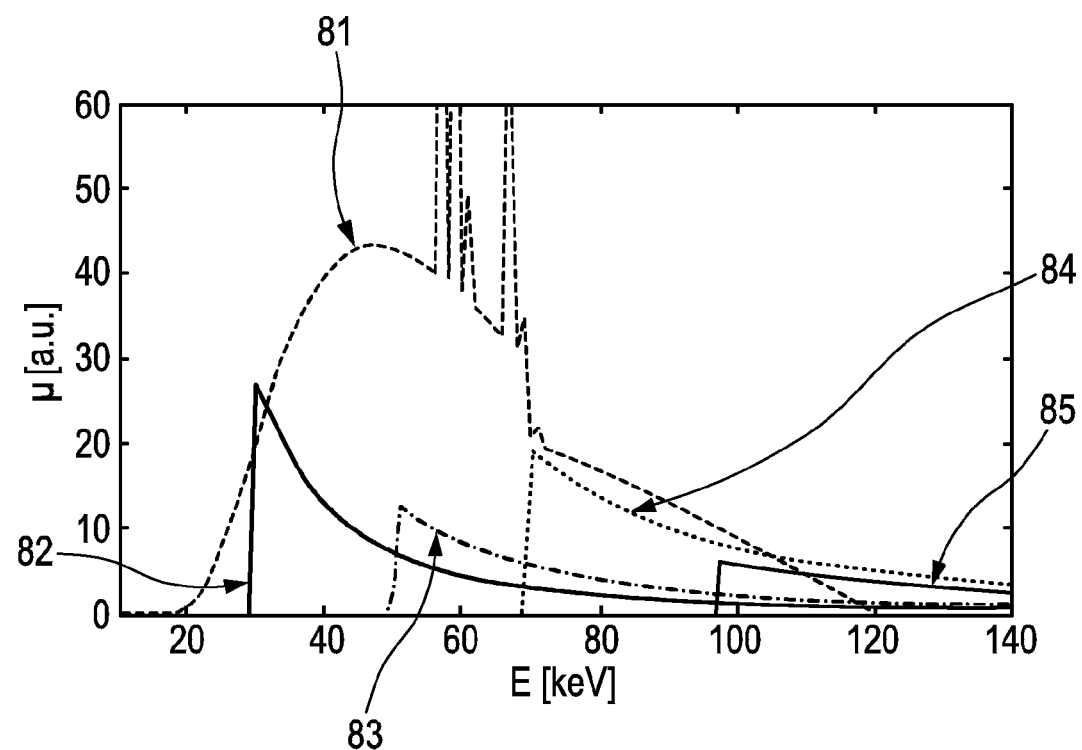
FIG. 12 illustrates schematically and exemplarily a spectrum of polychromatic radiation provided by an embodiment of the radiation device and K-shell contributions of attenuation spectra of different materials having K-edges at different energies.

The fluorescent elements 63 are used to probe the spectrum of the polychromatic radiation provided by the radiation device 2 with different spectral windows, i.e. to probe different spectral parts of the spectrum. This is schematically and exemplarily illustrated in FIG. 12 showing a filtered spectrum 81 of an x-ray tube and the energy dependence of K-shell contributions of the attenuation coefficients μ in arbitrary units for different fluorescent elements 63, wherein the line 82 relates to tin, the line 83 relates to gadolinium, the line 84 relates to tungsten and the line 85 relates to lead.

The K-edges of the fluorescent elements 63 should be in the energy range of the spectrum of the polychromatic radiation provided by the radiation device 2. Preferred fluorescent K-edge materials are gallium having a K-edge at 10.3 keV, germanium having a K-edge at 11.1 keV, niobium having a K-edge at 19.0 keV, silver having a K-edge at 25.5 keV, tin having a K-edge at 29.2 keV, barium having a K-edge at 37.4 keV, gadolinium having a K-edge at 50.2 keV, ytterbium having a K-edge at 61.3 keV, tantalum having a K-edge at 67.4 keV, tungsten having a K-edge at 69.5 keV, gold having a K-edge at 80.7 keV, lead having a K-edge at 88.0 keV, and bismuth having a K-edge at 90.5 keV. The fluorescent elements 63 can of course also comprise other fluorescent materials having a K-edge within the spectrum of the polychromatic radiation provided by the radiation device 2.

The fluorescent elements 63 are preferentially foils, which are relatively thin, for instance, which have a thickness of about 100 μm, and which are arranged at an angle of 45 degrees with respect to the primary beam 61 coming from the radiation device 2. Moreover, the fluorescence is preferentially detected under an angle of 90 degrees to the primary beam.

The reference values generation device 60 further comprises an energy-dependent reference values generation unit 66 for generating the energy-dependent reference values based on the generated fluorescence detection values. In particular, the energy-dependent reference values generation unit 66 is adapted to model a fluorescence detection value as an energy-integrated combination of a fluorescence yield $\omega_K$ of the respective fluorescent element, a linear absorption coefficient $\mu_K(E)$ for absorption by the photoeffect of the respective fluorescent element and the polychromatic radiation $\Phi(E)$ provided by the radiation device 2 and to determine the polychromatic radiation $\Phi(E)$ as energy-dependent reference values based on the model, known fluorescence yields $\omega_K$, known absorption coefficients $\mu_K(E)$ and the generated fluorescence detection values. Thus, the energy-dependent reference values generation unit 66 may be adapted to use following equation for determining the energy-dependent reference values:

$$Y_K = \int dE\, Y_K(E)\Phi(E) = \int dE\, \omega_K \mu_K(E)\Phi(E), \quad (1)$$

wherein $Y_K$ denotes the K-shell fluorescence yield of the respective fluorescent element, i.e. the respective fluorescence detection value being indicative of the fluorescent radiation from a respective K-edge element 63. The linear absorption coefficient for absorption by the photo-effect of a K-shell electron $\mu_k$ may be interpreted as the bin sensitivity of a given spectral channel.

Spectral imaging can improve, for instance, medical imaging. For example, a contrast agent may be better distinguished from tissue and/or different kinds of tissue may be better distinguished. For distinguishing these different materials the spectral computed tomography projection data are preferentially decomposed, wherein this decomposition depends on the spectrum of the polychromatic radiation provided by the radiation device. In order to provide this spectrum and also in order to monitor the x-ray tube output on short time scales, for instance, during one anode rotation, and on long time scales, in order to monitor a degradation of the anode, or to analyze different tracks on the anode, the reference values generation device 60 described above with reference to FIG. 11 may be used, wherein a conventional integrating detector technology, which can be used with high fluxes, is applied for finally determining intensities for different spectral channels, i.e. for finally generating energy-dependent reference values.

The generated energy-dependent reference values can be used for determining the origin of changes of the total photon output of the radiation device 2. These changes of the total photon output can be caused, for instance, by the electron production, beam shaping changes, changes in self absorption of the anode depending on the time, location and size of the focal spot on the anode, et cetera. If the changes of the total photon output are caused by electron production, they may be caused by instability of the voltage and/or current used for producing the electron beam or by cold emission. If the generated spectral reference values indicate that the output decreases in all spectral channels in the same way, it is unlikely that the anode absorption has increased, whereas, if the spectral output changes differently for the different spectral channels, it is likely that this change is caused by changes in the self absorption of the anode. Rules can be provided defining possible causes for changes of the total photon output based on the generated energy-dependent reference values, wherein these rules can be used by, for instance, the spectral parameter providing unit 12 or another unit of the spectral computed tomography system for determining the cause of the changes of the total photon output.

Figure 13:
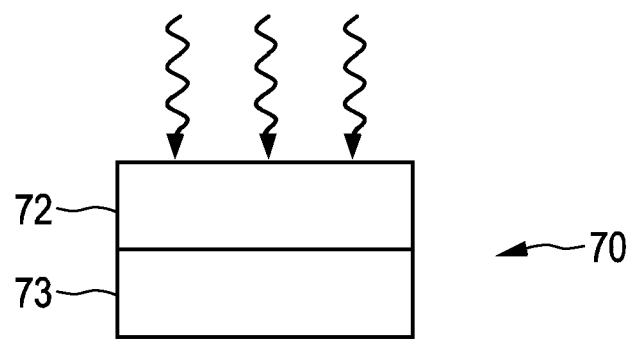
FIG. 13 shows schematically and exemplarily a further embodiment of a reference values generation device.

In a further embodiment a reference values generation device 70, which is schematically and exemplarily illustrated in FIG. 13, is used for generating the energy-dependent reference values based on the radiation provided by the radiation device 2, which has not traversed the examination zone 5. The reference values generation device 70 comprises a non-energy-resolving detector 72 for detecting the radiation, which has been provided by the radiation device 2 and which has not traversed the examination zone 5, and for generating non-energy-depending detection values based on the detected radiation. The reference values generation device 70 further comprises a reference values generation unit 73 for generating the energy-dependent reference values based on the generated non-energy-depending detection values, a known energy-bin-dependent number of photons $n_{0,b}$, a known energy-bin-dependent dead time $\tau_b$ of the spectral projection data generation device 6, a known energy-bin-dependent average linear attenuation coefficient $\mu_b$ and a known material thickness D. These energy-bin-dependent parameters are preferentially known from a previous calibration measurement, wherein the calibration measurement is preferentially performed in dependence of the respective pixel of the detector. For instance, they can be performed by scanning a water-like material for different thicknesses. The material thickness D is preferentially known from an estimation which is performed based on spatial projection data from an actual scan of an object to be imaged and the known energy-bin-dependent parameters $n_{0,b}$, $\tau_b$ and $\mu_b$.

The use of reference detectors in computed tomography is a state-of the art measure to pre-process scan raw data, i.e. projection data, in order to compensate for tube-output fluctuations or arching. The main idea is that a reference detector is placed somewhere close to the x-ray tube or close to the data-measurement-system (DMS), i.e. close to the projection data generation device, in order to sense time dependent fluctuations of tube output or sudden drops in intensity due to tube arching. As the reference detectors are usually of the scintillator type like the computed tomography detector itself, the assumption that the fluctuations picked up by the reference detector are indicative of the fluctuations picked up by the DMS itself is valid to an excellent extend. In other words, neglecting beam-hardening effects, if the measured intensity n on a certain detector pixel is related to the intensity in the source $n_0$ by Beer's law $$n = n_0 e^{-\mu D}, \quad (2)$$

the fluctuations in n and $n_0$ caused by fluctuating tube output are related by:

$$\frac{\delta n}{n} = \frac{\delta n_0}{n_0} \quad (3)$$

Hence, under the assumption that the tube output fluctuations are picked up in an identical manner by the reference detector ($\delta I/I$), the following correction of the raw data n for all pixels of the DMS can be performed based on the current reference detector reading:

$$\delta n = -\frac{\delta I}{I} n. \quad (4)$$

The minus sign indicates that a positive measured relative intensity fluctuation must give rise to a negative correction of the measured reading in the pixel.

Figure 14:
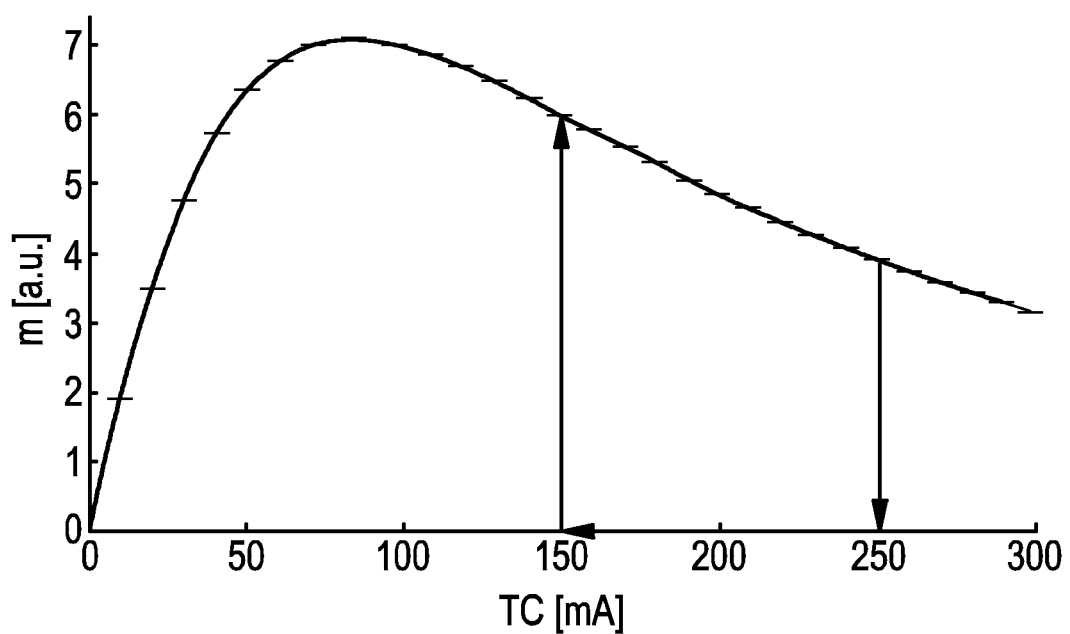
FIG. 14 illustrates a dependence of an output count rate of an energy-resolving photon-counting detector of an embodiment of the spectral projection data generation device on a tube current applied to an x-ray tube of an embodiment of the radiation device.

However, the procedure described above with reference to equations (2) to (4) does not only fail for energy-resolving photon-counting detectors subject to large levels of pile-up, but can easily be seen to make things worse by inspecting the dependence of a measured output count rate (OCR) of an energy-resolving photon-counting detector on the tube current applied to an x-ray tube as depicted in FIG. 14. In FIG. 14 m denotes the OCR in arbitrary units and TC denotes the tube current in mA. As it is clear from this figure, the x-ray intensity fluctuations $\delta I/I$ as picked up by an integrating, i.e. non-energy-resolving, reference detector cannot be used to correct the OCR for the entire dynamic range in a way similar as expressed in equation (4). For the case where the nominal tube output corresponds to 250 mA but an arcing event effectively renders the integrated intensity to only 150 mA, the current reference detector reading would suggest a correction of the current frame that would increase the current photon-counting detector reading (OCR) whereas the OCR would need to be corrected towards lower values as can be understood from FIG. 14. Hence, when integrating reference detectors are used in conjunction with an energy-resolving photon-counting DMS, there exists the need for a more sophisticated procedure.

The logged OCR $\ln(m_b)$ expected from an energy-resolving photon-counting detector as a function of logged source intensity $\ln(n_{0,b})$ and attenuation by a water-like absorber of length D and linear attenuation coefficient $\mu_b$ can be represented in a paralyzable, beam-hardening-free forward model for a one-sided energy bin via the relation:

$$\ln(m_b) = \ln(n_{0,b}) - \mu_b D - n_{0,b} \tau_b e^{-\mu_b D}, \quad (5)$$

where $\tau_b$ represents the effective dead time for a bin b. By taking the derivative of equation (5) with respect to $n_{0,b}$ fluctuation in the source output can be related to fluctuation in $m_b$ (OCR):

$$\frac{\delta m_b}{m_b} = \frac{\delta n_{0,b}}{n_{0,b}} (1 - n_{0,b} \tau_b e^{-\mu_b D}) \quad (6)$$

From this, following the assumption that the reference detector picks up changes in tube output in the same manner as the DMS itself (as assumed in the integrating computed tomography case exemplarily described with reference to equations (2) to (4)):

$$\frac{\delta n_{0,b}}{n_{0,b}} = \frac{\delta I}{I} \quad (7)$$

the required reference detector correction for this energy bin can immediately be obtained:

$$\frac{\delta m_b}{m_b} = -\frac{\delta I}{I} (1 - n_{0,b} \tau_b e^{-\mu_b D}) \quad (8)$$

By the minus sign in equation (8) again the fact is taken into account that measured fluctuation and correction have opposite signs (in the linear approximation regime). The right hand side of equation (8) may be regarded as defining energy-dependent reference values, i.e. energy-bin-dependent reference values, which are determined based on the generated non-energy-dependent detection values, the energy-bin-dependent number of photons $n_{0,b}$, the energy-bin-dependent dead time $\tau_b$, the energy-bin-dependent average linear attenuation $\mu_b$ and the material thickness D. Equation (8) is preferentially applied for each pixel of the detector independently, but with the same relative reading of the non-spectral reference detector. It can be used to correct for tube fluctuations in the presence of pile-up.

Equation (8) correctly takes the dependence of the OCR on the tube current, which is illustrated in FIG. 14, into account. For a low tube flux $n_{0,b}$ and/or detectors (or bins) with small dead times $\tau_b$ and/or large attenuation $\mu_b D$, the second term in parenthesis is negligible compared to unity and equation (8) reduces to equation (4) for the integrating case. This is the regime, where the counting detector reacts linearly to flux changes, as for currents below about 25 mA in FIG. 14. For a high tube flux $n_{0,b}$ and/or detectors (or bins) with large dead times $\tau_b$ and/or little to no attenuation $\mu_b D$, the second term in parenthesis in equation (8) dominates over the first term. In this latter case, the correction changes sign as expected. In (or slightly around) the singular case where the two terms cancel (close to the OCR maximum), tube fluctuations have no effect on $m_b$ and hence no correction needs to be applied.

One important difference in the reference detector normalization for energy-resolving photon-counting detectors expressed in equation (8) compared to equation (4) for the integrating case is that the average linear attenuation $\mu_b$, for the respective energy bin, the effective dead time $\tau_b$ and $n_{0,b}$ need to be known prior to the correction. This however, as already mentioned above, can easily be achieved and is typically obtained from a series of calibration scans of the water-like material for different lengths D. After the calibration $n_{0,b}$, $\tau_b$ and $\mu_b$ are known for all bins. If now a scan is performed, the bin raw data $\{n\}_b$, i.e. the spectral computed tomography projection data of an actual scan of an object to be imaged, can be used to estimate the effective material thickness D. Once D is known the reference detector correction can be applied for all energy bins and a new reconstruction can be performed. The above procedure can of course be repeated iteratively but is expected to converge very quickly.

Figure 15:
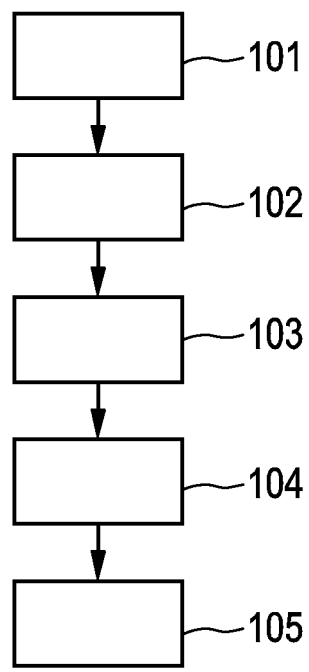
FIG. 15 shows a flowchart exemplarily illustrating an embodiment of a spectral computed tomography method.

In the following an embodiment of a spectral computed tomography method will exemplarily be described with reference to a flowchart shown in FIG. 15.

In step 101 polychromatic radiation, which traverses the examination zone 5, is provided by the radiation device 2 and spectral computed tomography projection data are generated based on the radiation after having traversed the examination zone 5 by the spectral projection data generation device 6, while the radiation device 2 rotates around an object to be imaged, which is arranged in the examination zone 5. Moreover, in step 101 energy-dependent reference values are generated based on radiation, which has been generated by the radiation device 2 and which has not traversed the examination zone 5, by the reference values generation device. In step 102 a spectral parameter being indicative of a spectral property of the radiation device 2 is determined based on the energy-dependent reference values by the spectral parameter providing unit 12 and in step 103 the correction unit 13 corrects the generated spectral computed tomography projection data based on the determined spectral parameter. For instance, as the spectral parameter a spatial and temporal distribution of energy-dependent reference values may be determined for positions, which correspond to positions at which the spectral computed tomography projection data have been generated, and for times, at which the spectral computed tomography projection data have been acquired, wherein this spatial and temporal distribution of energy-dependent reference values can be used for correcting the spectral computed tomography projection data. Or, the above-described K-edge-related ratios can be determined and used for correcting the spectral computed tomography projection data. In step 104 the corrected spectral computed tomography projection data are used by the reconstruction unit 14 for reconstructing a computed tomography image and in step 105 the reconstructed computed tomography image is shown on the display 16.

Steps 101 to 103 can also be regarded as being steps of a method for generating spectral computed tomography projection data. Moreover, the method can comprise further steps like outputting the determined spectral parameter and/or storing the determined spectral parameter, wherein the output and/or stored determined spectral parameter can be used for indicating a change of the spectral properties of the radiation device, which may require, for instance, a replacement of the radiation device.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the spectral parameter being indicative of a spectral property of the radiation device, the correction of the spectral computed tomography projection data based on the determined spectral parameter, the reconstruction of a computed tomography image, et cetera, performed by one or several units or devices can be performed by any other number of units or devices. These operations and/or the control of the computed tomography system in accordance with the computed tomography method and/or the control of the apparatus for generating spectral computed tomography projection data in accordance with the method for generating spectral computed tomography projection data can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for generating spectral computed tomography projection data. A spectral projection data generation device comprising an energy-resolving detector generates spectral computed tomography projection data based on polychromatic radiation, which has been provided by a radiation device, after having traversed an examination zone, and a reference values generation device generates energy-dependent reference values based on radiation, which has not traversed the examination zone. A spectral parameter providing unit provides a spectral parameter being indicative of a spectral property of the radiation device based on the energy-dependent reference values. In particular, spectral properties of the radiation device can be monitored over time, wherein this information can be used for, for instance, correcting the spectral computed tomography projection data, and/or, if undesired spectral properties of the radiation device are indicated, triggering a replacement of the radiation device.

The invention claimed is:

1. A system for generating spectral computed tomography projection data, the system comprising:
   a radiation device for providing polychromatic radiation for traversing an examination zone of the system,
   a spectral projection data generation device comprising an energy-resolving detector for generating spectral computed tomography projection data based on the radiation after having traversed the examination zone,
   a reference values generation device for generating energy-dependent reference values based on radiation, which has not traversed the examination zone, and
   a spectral parameter providing unit for providing a spectral parameter being indicative of a spectral property of the radiation device based on the energy-dependent reference values.

2. The system as defined in claim 1, wherein the system further comprises a correction unit for correcting the generated spectral computed tomography projection data based on the determined spectral parameter.

3. The system as defined in claim 1, wherein the reference values generation device comprises an energy-resolving reference detector for detecting the radiation and for generating the energy-dependent reference values depending on the detected radiation.

4. The system as defined in claim 3, wherein the energy-resolving detector of the spectral projection data generation device and the energy-resolving reference detector are of the same type.

5. The system as defined in claim 3, wherein the radiation device comprises a radiation source for emitting the polychromatic radiation and a collimator for collimating the emitted polychromatic radiation, wherein the energy-resolving reference detector is arranged between the radiation source and the collimator.

6. The system as defined in claim 1, wherein the reference values generation device comprises a K-edge element having a K-edge at an energy within the spectrum of the polychromatic radiation provided by the radiation device, wherein the reference values generation device and the radiation device are arranged such that polychromatic radiation emitted by the radiation device impinges on the K-edge element, wherein the reference values generation device is adapted to generate the energy-dependent reference values based on the radiation coming from the K-edge element.

7. The system as defined in claim 6, wherein the reference values generation device comprises an energy-resolving reference detector, wherein the reference values generation device and the radiation device are arranged such that the radiation, which has traversed the K-edge element and hence which has been filtered by the K-edge element is detectable by the energy-resolving reference detector, wherein the energy-resolving reference detector is adapted to generate the energy-dependent reference values based on the detected radiation.

8. The system as defined in claim 7, wherein the reference values generation device comprises several K-edge elements with K-edges at different energies, which are within the spectrum of the polychromatic radiation provided by the radiation device, for filtering the radiation before being detected by the energy-resolving reference detector, wherein the spectral parameter providing unit is adapted to a) determine the spectral parameter based on spectral reference values at the energies, at which the K-edges are present, and/or b) calculate one or several summed values by summarizing spectral reference values for energies being smaller than the lowest energy, at which a K-edge is present, and/or for energies between energies, at which different K-edges are present, and/or for energies being larger than the largest energy, at which a K-edge is present, and to determine the spectral parameter based on the one or several summed values.

9. The system as defined in claim 1, wherein the reference values generation device is adapted to generate energy-dependent reference values for different positions and/or times, wherein the spectral parameter providing unit is adapted to calculate as the spectral parameter a spatial and/or temporal distribution of energy-dependent reference values based on the generated energy-dependent reference values.

10. The system as defined in claim 1, wherein the reference values generation device comprises:
    different fluorescent elements for emitting fluorescent radiation when the polychromatic radiation impinges on the fluorescent elements,
    several non-energy-resolving reference detectors assigned to the different fluorescent elements, in order detect the fluorescent radiation and generate fluorescence detection values based on the detected fluorescent radiation, and
    an energy-dependent reference values generation unit for generating the energy-dependent reference values based on the generated fluorescence detection values.

11. The system as defined in claim 10, wherein the energy-dependent reference values generation unit is adapted to model a fluorescence detection value as an energy-integrated combination of a fluorescence yield $\omega_K$ of the respective fluorescent element, a linear absorption coefficient $\mu_K(E)$ for absorption by the photoeffect of the respective fluorescent element and the polychromatic radiation $\Phi(E)$ provided by the radiation device and to determine the polychromatic radiation $\Phi(E)$ as energy-dependent reference values based on the model, known fluorescence yields $\omega_K$, known absorption coefficients $\mu_K(E)$ and the generated fluorescence detection values.

12. The system as defined in claim 1, wherein the reference values generation device comprises:
    a non-energy-resolving detector for detecting the radiation, which has been provided by the radiation device and which has not traversed the examination zone, and for generating non-energy-depending detection values based on the detected radiation, and
    a reference values generation unit for generating the energy-dependent reference values based on the generated non-energy-depending detection values, a known energy-dependent number of photons $n_{0,b}$, a known energy-dependent dead time $\tau_b$ of the spectral projection data generation device, a known energy-dependent average linear attenuation $\mu_b$ and a known material thickness D.

13. A spectral computed tomography system comprising:
    a system for generating spectral computed tomography projection data as defined in claim 1, and
    a reconstruction unit for reconstructing an image based on the generated spectral computed tomography projection data.

14. A method for generating spectral computed tomography projection data for a computed tomography system, the method comprising:
  providing polychromatic radiation for traversing an examination zone of the system by a radiation device,
  generating spectral computed tomography projection data based on the radiation after having traversed the examination zone by a spectral projection data generation device comprising an energy-resolving detector,
  generating energy-dependent reference values based on radiation, which has been generated by the radiation device and which has not traversed the examination zone, by a reference values generation device, and
  providing a spectral parameter being indicative of a spectral property of the radiation device based on the energy-dependent reference values by a spectral parameter providing unit.

15. A non-transitory computer program for controlling a system for generating spectral computed tomography projection data, the computer program comprising program code means for causing the system to carry out the steps of the method for generating spectral computed tomography projection data as defined in claim 14, when the computer program is run on a computer controlling the system.

* * * * *